United States Patent [19]

Ingram, Jr. et al.

[11] Patent Number: 5,267,860
[45] Date of Patent: Dec. 7, 1993

[54] DENTAL HYGIENE TOOL WITH SHIELD AND GERMICIDAL SEALS

[76] Inventors: William L. Ingram, Jr., 350 S. Lake Ave., #250, Pasadena, Calif. 91101; Ghassan A. Alireza, 815 Fairfield Cir., Pasadena, Calif. 91106

[21] Appl. No.: 937,494

[22] Filed: Aug. 28, 1992

[51] Int. Cl.$^5$ .......................... A61C 1/16; A61C 1/05
[52] U.S. Cl. .................................... 433/116; 433/115
[58] Field of Search ............... 433/115, 116, 125, 166

[56] References Cited

U.S. PATENT DOCUMENTS

| | | |
|---|---|---|
| 1,485,963 | 3/1924 | Curry . |
| 1,691,823 | 11/1928 | Ogilvie . |
| 2,073,137 | 3/1937 | Bimrose ............... 433/116 |
| 3,542,372 | 11/1970 | Edwardson ........... 433/116 X |
| 3,758,948 | 9/1973 | Bareth .................. 433/115 |
| 4,266,935 | 5/1981 | Hoppe . |
| 4,295,830 | 10/1981 | Uchida ................. 433/115 |
| 4,369,034 | 1/1983 | Garnier et al. ....... 433/115 |
| 4,446,967 | 5/1984 | Halkyard . |
| 4,693,871 | 9/1987 | Geller . |
| 4,723,912 | 2/1988 | Nieusma ............... 433/116 |
| 4,728,290 | 3/1988 | Eisner et al. . |
| 4,752,223 | 6/1988 | Carlson . |
| 4,789,336 | 12/1988 | Lewis ................... 433/116 |
| 4,795,343 | 1/1989 | Choisser ............... 433/116 |
| 4,975,056 | 12/1990 | Eibofner .............. 433/115 X |
| 5,074,788 | 12/1991 | Nakanishi ............. 433/115 |

*Primary Examiner*—Gene Mancene
*Assistant Examiner*—Nicholas D. Lucchesi
*Attorney, Agent, or Firm*—Christie, Parker & Hale

[57] ABSTRACT

An extendable latex shield and internal seals are incorporated in a disposable dental hygiene tool for protecting sterility of standard dental handpieces. The flexible nature of the extendable shield allows storage in a first position, permitting the dental professional to easily attach the tool to the handpiece and to unroll the flexible shield to the extended position, thereby protecting the handpiece from splashing of saliva, blood, or other materials during use of the tool in dental procedures. Internal seals in the tool preclude fluids or other material from transfer through the interior of the tool into the dental handpiece. The combination of the present device precludes the contamination of the handpiece, thereby avoiding sterilization procedures and the inherent time loss, inefficiency, and cost associated with such procedures.

6 Claims, 1 Drawing Sheet

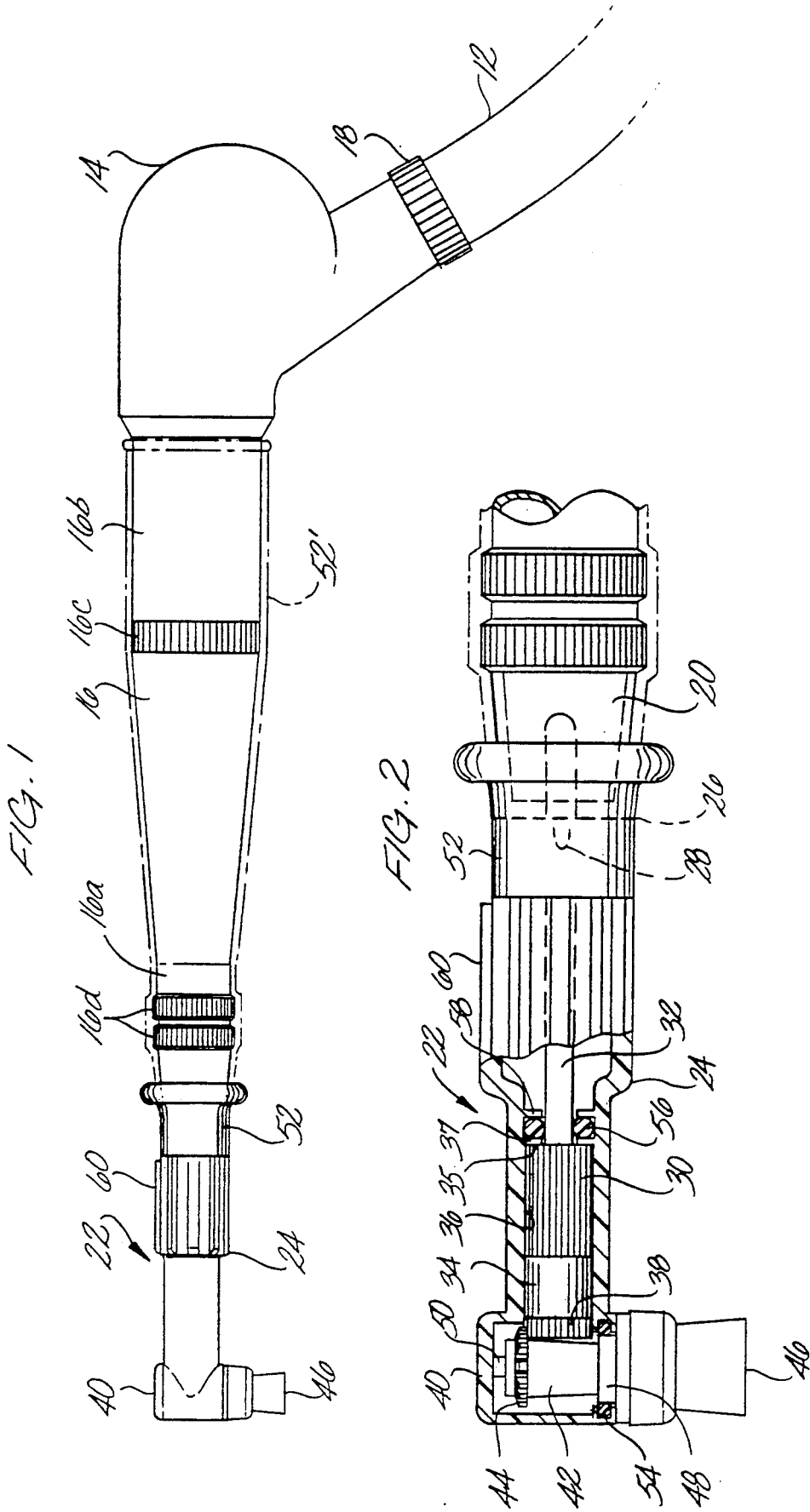

DENTAL HYGIENE TOOL WITH SHIELD AND GERMICIDAL SEALS

FIELD OF THE INVENTION

This invention relates generally to the field of instruments for professional dental hygiene, including cleaning and polishing of teeth. More particularly, the present invention provides a disposable attachment for standard dental handpieces which incorporates internal seals and an external extendable shield to prevent contamination of the motorized handpiece to which the tool is attached for dental procedures.

1. Background of the Invention

Dental tools, by the nature of their use, are easily contaminated by saliva or blood of the patient during work by the dentist or dental technician. Further, dental tools and the handpieces to which they connect for power and manipulation are relatively complex pieces of machinery built to close tolerances. Contamination has typically been dealt with by the design of tools and handpieces for separation of the tools to allow individual sterilization or disposal separate from the handpiece. The potential for contamination of the handpiece, however, requires separate cleaning or sterilization.

Recent health concerns due to the rise in Acquired Immune Deficiency Syndrome (AIDS) has created the need for greater care in assuring that dental instruments are not contaminated for the protection of both patients and professionals using the instruments. Disposable dental tools, particularly for tools used in dental hygiene such as cleaning and polishing of a patient's teeth assures that no contamination will be created by reuse of the tool. Exemplary of this type of tool are disposable prophy angles such as those sold under the trademark DENTICATOR ®, produced by the Denticator Co., Inc., and described in U.S. Pat. No. 3,727,313; VANTAGE ®; or RITE-ANGLE TM, produced by Ash Dentsply. These devices are primarily constructed of various plastic materials to reduce expense and are entirely disposable.

Alternatively, removable dental tools such as prophy angles may be manufactured for easy sterilization due to the relatively small size and limited complexity of the tool itself. Difficulties in assuring adequate sterilization of such tools are present and typically autoclaving is required. Degradation of the tools due to high temperatures encountered in autoclaving limits the life of such tools or adds requirements for lubrication or other maintenance.

Disposability or sterilization of tools such as prophy angles does not eliminate the potential for contamination of the handpiece, which holds the tool for use and provides power to the tool for operation. Dental handpieces are extremely complex and not amenable to autoclaving due to their size and requirements for disassembly. Further, degradation of such handpieces caused by sterilizing procedures makes the end cost of such use unacceptable. In addition, the requirement for sterilizing the handpiece between each use requires availability of a large number of handpieces to adequately accommodate patients in a regular office schedule.

Protective devices for handpieces have been developed as exemplified by U.S. Pat. Nos. 4,752,223 to Carlson; No. 4,728,290 to Eisner, et al.; No. 4,693,871 to Geller; and No. 4,266,935 to Hoppe. Carlson discloses a sanitary sheath for use with a dental handpiece which requires a removable mountable clip mounted to the handpiece for maintaining the sheath in alignment with the operative openings of the dental handpiece. Eisner similarly provides a protective covering employed in cooperation with a dental tool carrier and tightening and release mechanism tool for attachment and release of dental tools while employing the protective covering on a hand tool. Geller discloses a vacuum formed thermoplastic sheath with openings positioned for tool mating with the dental handpiece, and Hoppe provides a sterilized protective sheath having an elastic tubular casing employing a shape retaining hard synthetic resin plate for alignment with the bore in the hand tool.

Each of these devices includes openings through which contamination may be transmitted to the handpiece and further requires complex retaining mechanisms or fabrication techniques to assure alignment of all openings required for operation of the tool with the handpiece.

In addition, disposable tools such as prophy angles, as presently designed, provide the potential for contamination of the dental handpiece through transmission of saliva or blood internal to the disposable tool as well as splashing of blood or saliva beyond the disposable tool and onto the handpiece.

The present invention eliminates the deficiencies of the devices referenced to provide in combination a disposable tool incorporating protection for the handpiece and eliminating the potential for internal contamination of the handpiece.

SUMMARY OF THE INVENTION

The present invention is a dental hygiene tool incorporating a low cost plastic barrel portion having a first opening for engaging the dental handpiece and a head mounted to the barrel portion distal the first opening to rotatably carry a cleaning cup for prophy paste or other appliance. An axle carried within the barrel portion incorporates a tang received in the drive chuck of the handpiece and a drive gear for transmission of power from the axle. The tool head carries a second rotating axle having a mating gear engaging the drive gear of the first axle. The cup or other appliance is attached to the second axle opposite the mating gear to extend from the tool head.

A latex sheath sealingly affixed at a first end to the external surface of the barrel portion provides an extendable covering for the handpiece which is unrolled over the interface of the barrel portion with the handpiece and substantially the entire handpiece thereby precluding external contamination of the handpiece. A first O-ring carried internally by the tool head engages the second axle in a friction fit to provide a seal preventing transmission of saliva, blood, or other fluids through the interior of the tool head. A second O-ring carried internal to the barrel portion engages the first axle with a friction fit to provide a second seal precluding transmission of any fluids or materials penetrating the first O-ring in the tool head from being transmitted through the barrel portion to the drive chuck or interior of the handpiece.

A germicidal gel coating on the first and second O-rings provides additional defense against transmission of viral or bacterial matter through the O-ring seals.

Upon completing use of the tool, the invention, including the barrel portion, tool head and extendable sheath, is removed from the handpiece and disposed of in a proper manner, thereby precluding any contamination of the handpiece which could be transmitted to the next patient or dental professional.

DESCRIPTION OF THE DRAWINGS

FIG. 1 is a pictorial side view of the present invention mounted to a dental handpiece showing the extendable shield in a rolled position with the extended unrolled position shown in phantom.

FIG. 2 is a partial cut-away side view demonstrating the axles and O-rings incorporated in the invention and attachment of the device to the dental handpiece.

DETAILED DESCRIPTION

The embodiment of the invention shown in the drawings is employed with standard low speed dental handpieces 10 as represented generally in FIG. 1. A dental handpiece incorporates a rotating power transmission cable 12 attaching to a planetary gear of other transmission arrangement 14 in the base of the handpiece a handle 16 provides a grasping surface for the operator to use the handpiece and internally carries drive means for transmitting power from the planetary gears. A standard knurled nut and threaded attachment 18 is employed for removable attachment of the power cable to the handpiece and the handpiece incorporates disassemble sections 16A and 16B for cleaning and maintenance of the drive means within the handle. Knurled grips 16C and 16D are provided to improve the operators grip on the handpiece and for use in disassembling the sections.

As best seen in FIG. 2, the handpiece incorporates a chuck 20 for transmitting rotational power from the handpiece to the tool employed. Standard handpieces provide a slip fit arrangement for attachment of a tool to the handpiece with key slots for securing and orienting the tool.

The dental hygiene tool 22 incorporating the present invention, as shown in the drawings, incorporates a first barrel portion 24 having an open end 26 which is received in a slip fit arrangement on the handpiece. A key slot 28 in the barrel receives a key on the handpiece for alignment of the tool to provide proper orientation for use with the handpiece and to prevent rotation of the barrel on the handpiece during its use. A first axle 30 is carried within the barrel portion and terminals at a first end in a tang 32 which is received within the chuck of the handpiece. Power transmitted from the flexible cable to the handpiece and through the handpiece is provided to the axle by rotation of the chuck. The axle in the embodiment shown in the drawings is supported within the barrel portion by a slip ring 34 providing a bearing surface riding on the inner cylindrical surface 36 of the barrel portion. A shoulder 35 on the first axle contacts a protrusion 37, on the inner circumference of the barrel to constrain longitudinal motion of the axle within the barrel portion. The first axle terminates opposite the tang in a drive gear 38 for transmitting the rotational motion from the chuck through the axle.

A tool head 40 extends from the barrel portion opposite the open end attachment for the handpiece. The tool head encloses a second axle 42 which incorporates a mating gear 44 which engages the drive gear on the first axle. In the embodiment shown in the drawing the positioning of the two axles and the associated gears provides a 90° angle for driving the rubber cup 46 comprising the appliance for cleaning or polishing teeth. This appliance typically comprises a fluted rubber cup for containing prophy paste, however, alternate appliance arrangements may be employed using the present invention.

The second axle incorporates a slip ring 48 which bears on the cylindrical inner surface of the tool head acting as a bearing for rotational motion of the second axle. A pin 50 integral with the inner upper surface of the tool head is received in an axial depression (not shown) in the second axle to further constrain motion of the second axle within the tool head. The arrangement of the drive gear and mating gear, as shown in FIG. 2, provides structural support urging the second axle onto the pin thereby preventing longitudinal motion of the second axle.

The barrel portion and tool head of the embodiment of the invention shown in the drawings is molded using standard injection molding techniques for ABS, polyethylene or other rigid plastic. Fabrication of the axles from teflon, nylon, or similar materials provides a low friction interface for the slip rings with the inner surfaces of the molded barrel and tool head, thereby eliminating the requirement for complex bearing assemblies.

An extendable sheath 52 fabricated from flexible latex rubber in the embodiment shown in the drawings is attached to the exterior cylindrical surface of the barrel portion proximate the open end of the barrel attaching to the handpiece. In a presently preferred embodiment, the latex sheath is adhesively bonded to the external cylindrical surface of the barrel portion. In alternative embodiments, a thermal bond or elastic fit with mechanical restraining means are employed for attachment of the sheath to the barrel portion. Flexibility of the sheath allows storage in a rolled position shown in the drawings. In this position the open end of the barrel portion of the tool is visible for ease of attachment to the handpiece. Upon attachment of the invention to the handpiece, the latex shield is unrolled to extend over the handpiece as shown by phantom 52'. The length of the sheath is adjustable in varying embodiments for handpieces of differing size and may be sufficient to cover the transmission means and other portions of the handpiece in addition to the handle. Flexibility of the latex sheath accommodates handpiece having varying angles and differing diameters of the handle are accommodated by elasticity in the cylindrical sheath. A thin walled latex sheath allows the dental professional to use the handpiece with normal tactile response.

The present invention prevents contamination of the dental handpiece through transmission of saliva, blood or other materials internal to the tool head and barrel portion through the use of a two barrier seal. A first O-ring 54 is constrained within the tool head for friction contact with the second axle, thereby providing a seal preventing fluids from being transmitted from the exterior of the tool and the prophy cup or other appliance through the interior spaces of the tool head. A second O-ring 56 is constrained in the barrel portion for frictional contact with the first axle thereby providing a second seal to prevent any fluids or materials penetrating the first O-ring from reaching the handpiece through the interior of the barrel portion. In the embodiment shown in the drawings, the second O-ring is constrained between the protrusion 37 and an additional protrusion 58 on the interior circumference of the barrel portion. Similar protrusions on the interior of the tool head constrain the first O-ring in contact with the second axle. Those skilled in the art will recognize alternative embodiments for grooving of the interior surface of the tool head and barrel portion for constraining the O-rings therein.

Prior to insertion in the invention, one or both of the O-rings are coated with a germicidal gel to provide additional protection against transmission of bacterial or viral contaminants present in the saliva, blood or other materials emanating from the patient or the dental procedure being performed. The gel provides additional mechanical barrier to transmission of the fluids and lubrication for rotation of the axles within the O-rings. In alternative embodiments, other sealing means are employed as replacements for the O-rings. Exemplary of such sealing means would be brush seals or close tolerance flanges surrounding the axles, the flanges or axle provided with integral grooves to contain the germicidal gel.

In the embodiment of the invention shown in the drawings, protruding ribs 60 are provided on the exterior of the barrel portion providing a grip to assist the dental professional in attaching the dental hygiene tool to the handpiece and as a gripping surface during use of the dental hygiene tool in combination with the handpiece.

Upon completion of hygiene procedures on a patient, the dental hygiene tool of the present invention is removed from the handpiece for disposal. Disconnection of the barrel portion from the handpiece may be accomplished with the latex shield in the rolled or unrolled position and the entire dental hygiene tool with shield is disposable. The extended shield precludes external contamination of the handpiece during hygiene procedures leaving the handpiece ready for immediate use with the next patient.

Having described the invention in detail as required by the patent statutes, those skilled in the art will recognize modifications and substitutions for elements of the embodiment disclosed. Such substitutions and modifications fall within the intent and scope of the present invention as defined by the following claims.

What is claimed is:

1. A disposable dental hygiene tool for use with a mechanical drive dental handpiece, the tool comprising:
   a plastic barrel portion having a first opening with orientation indices for engaging the dental handpiece and a tool head mounted to the barrel portion distal the first opening to rotatably carry a hygiene appliance; and
   a flexible sheath sealingly affixed circumferentially at a first end to an external surface of the barrel portion intermediate said first opening and said tool head, said sheath carried in a first position conforming to the barrel portion and exposing said barrel portion proximate the first opening to allow visual perception of engagement of the barrel portion and the dental handpiece, said sheath deployable to a second position extending from said barrel portion to cover the dental handpiece.

2. A disposable dental hygiene tool as defined in claim 1 further comprising:
   a first drive means carried within the barrel portion for transmitting rotation from a chuck in the handpiece;
   a second drive means carried within the tool head and engaging the first drive means and the hygiene appliance for transmitting rotation from the first drive means to the appliance;
   a first sealing means for a rotational seal between the second drive means and an inside surface of the tool head, thereby preventing fluid passage between the second drive means and tool head; and
   a second sealing means for a rotational seal between the first drive means and an inside surface of the barrel portion, thereby preventing fluid passage between the first drive means and the barrel portion.

3. A disposable dental hygiene tool as defined in claim 2 wherein the first sealing means is coated with a germicidal gel.

4. A disposable dental hygiene tool as defined in claim 2 wherein the second sealing means is coated with a germicidal gel.

5. A disposable dental hygiene tool as defined in claim 2 wherein the first drive means comprises a first axle and the second sealing means comprises an O-ring frictionally engaging the first axle and an inner surface of the barrel portion.

6. A disposable dental hygiene tool as defined in claim 5 wherein the second drive means comprises a second axle and the first sealing means comprises an O-ring frictionally engaging the second axle and an inner surface of the tool head.

* * * * *